US007939015B1

(12) United States Patent
Elrod

(10) Patent No.: US 7,939,015 B1
(45) Date of Patent: May 10, 2011

(54) METHOD OF DESCENTING HUNTER'S CLOTHING

(75) Inventor: Scott Elrod, Angleton, TX (US)

(73) Assignee: Parah, LLC, Angleton, TX (US)

(*) Notice: Subject to any disclaimer, the term of this patent is extended or adjusted under 35 U.S.C. 154(b) by 280 days.

(21) Appl. No.: 11/018,620

(22) Filed: Dec. 21, 2004

(51) Int. Cl.
A61L 9/00 (2006.01)
A61L 2/00 (2006.01)
A61L 2/18 (2006.01)
A62B 7/08 (2006.01)

(52) U.S. Cl. ............... 422/5; 422/28; 422/29; 422/120; 422/123

(58) Field of Classification Search ............... 422/5, 28, 422/29, 120, 123
See application file for complete search history.

(56) References Cited

U.S. PATENT DOCUMENTS

| 1,961,878 | A | | 6/1934 | Gilkey | 423/210 X |
| 2,203,188 | A | | 6/1940 | Beer | |
| 3,214,364 | A | * | 10/1965 | Van Tuyle et al. | 422/186.19 |
| 3,421,836 | A | | 1/1969 | Sundin et al. | |
| 3,750,556 | A | | 8/1973 | Duke | |
| 3,937,967 | A | | 2/1976 | Steinitz | |
| 3,949,056 | A | | 4/1976 | Nakshbendi | 423/210 |
| 4,045,316 | A | | 8/1977 | Legan | |
| 4,238,857 | A | | 12/1980 | Waters | |
| 4,309,388 | A | | 1/1982 | Tenney et al. | |
| 4,374,571 | A | * | 2/1983 | Hirvela | 239/36 |
| 4,811,159 | A | | 3/1989 | Foster, Jr. | 361/231 |
| 4,863,687 | A | | 9/1989 | Stevens et al. | |
| 4,867,052 | A | | 9/1989 | Cipelletti | |
| 4,904,289 | A | | 2/1990 | Miyakami et al. | |
| 4,941,270 | A | | 7/1990 | Hoffman | |
| 4,953,674 | A | | 9/1990 | Landes | |
| 4,990,311 | A | | 2/1991 | Hirai et al. | |
| 5,087,426 | A | | 2/1992 | Inoue et al. | |
| 5,185,129 | A | | 2/1993 | Koutrakis et al. | |
| 5,192,500 | A | | 3/1993 | Treddenick | |
| 5,316,182 | A | | 5/1994 | Lee et al. | |
| 5,383,236 | A | | 1/1995 | Sesselmann | 2/243.1 |
| 5,429,271 | A | * | 7/1995 | Porter | 222/3 |
| 5,433,230 | A | | 7/1995 | Miller | |
| 5,433,919 | A | | 7/1995 | Baltes | |
| 5,468,454 | A | | 11/1995 | Kim | |
| 5,484,472 | A | | 1/1996 | Weinberg | |
| 5,514,345 | A | | 5/1996 | Garbutt et al. | |
| 5,520,893 | A | | 5/1996 | Kasting, Jr. et al. | 422/305 |
| 5,539,930 | A | | 7/1996 | Sesselmann | |
| 5,547,476 | A | | 8/1996 | Siklosi et al. | |
| 5,667,564 | A | | 9/1997 | Weinberg | |
| 5,681,355 | A | | 10/1997 | Davis et al. | |
| 5,762,648 | A | | 6/1998 | Yeazell | |
| 5,766,560 | A | | 6/1998 | Cole | |
| 5,789,368 | A | | 8/1998 | You et al. | |
| 5,790,987 | A | | 8/1998 | Sesselmann | |
| 5,833,740 | A | | 11/1998 | Brais | |
| 5,835,840 | A | * | 11/1998 | Goswami | 422/186.3 |
| 5,891,391 | A | | 4/1999 | Fore | 422/5 |
| 5,911,957 | A | | 6/1999 | Khatchatrian et al. | |
| 5,931,014 | A | | 8/1999 | Cole | |
| 5,983,834 | A | | 11/1999 | Tai | |
| 6,007,770 | A | | 12/1999 | Peiper et al. | |
| 6,009,559 | A | | 1/2000 | Sesselmann | |
| 6,094,549 | A | | 7/2000 | Hiraoka et al. | |
| 6,134,718 | A | | 10/2000 | Sesselmann | |
| 6,134,806 | A | * | 10/2000 | Dhaemers | 34/404 |
| 6,149,038 | A | | 11/2000 | Tsai | |
| 6,153,111 | A | * | 11/2000 | Conrad et al. | 210/741 |
| 6,156,268 | A | | 12/2000 | Curry et al. | |
| 6,163,098 | A | | 12/2000 | Taylor et al. | |
| 6,182,671 | B1 | * | 2/2001 | Taylor et al. | 132/116 |
| 6,284,204 | B1 | | 9/2001 | Cole et al. | |
| 6,312,507 | B1 | | 11/2001 | Taylor et al. | |
| 6,336,964 | B1 | | 1/2002 | Omatsu et al. | |
| 6,340,447 | B2 | | 1/2002 | Johnson | 422/5 |
| 6,340,497 | B2 | | 1/2002 | Wilson | |
| 6,355,216 | B1 | | 3/2002 | Kristiansson et al. | |
| 6,379,435 | B1 | | 4/2002 | Fukunaga et al. | |
| 6,503,547 | B1 | | 1/2003 | Lima | |
| 6,564,591 | B2 | | 5/2003 | Noyes | |
| 6,565,805 | B2 | | 5/2003 | Khatchatrian et al. | |
| 6,576,190 | B1 | | 6/2003 | Park | |
| 6,613,277 | B1 | | 9/2003 | Monagan | |
| 6,630,105 | B1 | * | 10/2003 | O'Neill et al. | 422/24 |
| 6,632,407 | B1 | | 10/2003 | Lau et al. | |
| D486,357 | S | | 2/2004 | Leba et al. | |

(Continued)

FOREIGN PATENT DOCUMENTS

| EP | 0261987 | | 3/1988 |
| JP | 06-327749 | A | 11/1994 |
| JP | 1109948 | A | 1/1999 |
| JP | 11009949 | A | 1/1999 |
| JP | 11226106 | A | 8/1999 |
| JP | 11226108 | A | 8/1999 |
| JP | 2003001237 | A | 1/2003 |
| JP | 2003024426 | A * | 1/2003 |
| WO | WO 0151096 | | 7/2001 |
| WO | WO03089017 | | 10/2003 |
| WO | WO 2004067043 | | 8/2004 |
| WO | 2005077425 | A1 | 2/2005 |
| WO | WO2005021135 | | 3/2005 |

OTHER PUBLICATIONS

Provisional U.S. Appl. No. 60/543,505, filed Feb. 11, 2004.*
English machine translation of JP 2003024426.*
English Abstract for JP 06 327749A, Inventor: Masuda.

Primary Examiner — Sean Conley
Assistant Examiner — Regina Yoo
(74) Attorney, Agent, or Firm — Holland & Hart

(57) ABSTRACT

A method for removing the human scent and any other scent that is not advantageous to the environment you are in from clothing and equipment used by sportsmen by the use of gaseous ozone or hydroxyl and hydroperoxide ions. The gas is applied directly or indirectly to the clothing, equipment and body while the hunter is in the field and/or prior to or after the hunt. The method can also be used by fishermen to eliminate fish odor. The method of delivering a gas in compressed/generated form from a container.

18 Claims, No Drawings

U.S. PATENT DOCUMENTS

| | | | |
|---|---|---|---|
| 6,896,853 B2 | 5/2005 | Lau et al. | 422/186 |
| 7,117,687 B2 | 10/2006 | Naaman | |
| 7,118,608 B2 | 10/2006 | Lovell | |
| 7,222,634 B2 | 5/2007 | Hess et al. | |
| 7,662,636 B2 | 2/2010 | Maruo et al. | |
| 2002/0030022 A1 | 3/2002 | Bradley | |
| 2002/0071795 A1* | 6/2002 | Jensen | 422/186.12 |
| 2002/0094298 A1* | 7/2002 | Monagan | 422/5 |
| 2003/0044308 A1 | 3/2003 | Toth | 422/5 |
| 2004/0047775 A1* | 3/2004 | Lau et al. | 422/186.04 |
| 2004/0149329 A1* | 8/2004 | Hess et al. | 135/156 |
| 2004/0221396 A1* | 11/2004 | Johnson | 8/115.51 |
| 2005/0186108 A1* | 8/2005 | Fields | 422/4 |
| 2006/0006122 A1* | 1/2006 | Burns et al. | 210/758 |
| 2006/0096331 A1 | 5/2006 | Kim | |
| 2007/0092414 A1 | 4/2007 | Malyon | |
| 2007/0166186 A1* | 7/2007 | Stec | 422/5 |
| 2007/0212253 A1 | 9/2007 | Elrod | |
| 2010/0071633 A1 | 3/2010 | Elrod | |
| 2010/0107991 A1 | 5/2010 | Elrod | |

\* cited by examiner

METHOD OF DESCENTING HUNTER'S CLOTHING

FIELD OF THE INVENTION

The invention relates to a method of de-scenting the clothes and apparatus of sportsmen, both professional, non professional, bikers, campers and the like. More particularly, there is provided a method of removing human scent and any other scent that is not advantageous in that environment from clothing and equipment of hunters and fish odors from fishermen utilizing an oxidizing agent which is ozone or a combination of hydroxyl and hydroperoxide ions.

BACKGROUND OF THE INVENTION

Animals have an acute sense of smell and are capable of recognizing a human scent or any other scent that is not advantageous in that environment at long distances. To avoid such recognition a hunter will attempt to stay down wind of the animal being hunted. The more common method used by hunters to trick the animals is to mask the human odor utilizing an animal scent. Unfortunately the animal scents which are utilized, are obnoxious and linger on the clothing for long periods of time. Some of the scents utilized include animal urine. A hunter who is camping overnight does not desire the animal scents to be carried over to bedtime, home, car, etc.

There are other drawbacks in utilizing animal scents or any other scents. The scent may attract a predator of the game which the hunter is not hunting for which the hunter may not be prepared to encounter. Descenting packs or containers containing food or any other substance that contains scents that may not be natural to the given environment. Also, the weapon used by the hunter has an odor recognizable by some animals which cannot be disguised with a scent.

Fishermen have the problem of fish odor on their hands and clothes which is difficult to remove. For fishermen camping overnight the fish odor is not only undesirable because of the odor but can also attract animals such as bears which the fishermen is not prepared to meet.

Hunters have prepared their clothing before hand by washing to remove prior scents and/or human odor. The washing materials may also leave an odor. However, out in the field the hunter can sweat and permeate the clothing with a human scent. It would be desirable to deodorize clothing during a hunt or while on a fishing trip.

Ozone has been used for decontaminating buildings and for decolorizing denim garment. U.S. Pat. No. 5,833,740 to Brais discloses an apparatus for sterilizing bottles utilizing ozone. The reference recognizes that ozone in large quantities can be harmful or irritating. Consequently, it was necessary to provide means for decomposing the excess ozone and/or to cause its escape into the atmosphere.

Ozone is a powerful oxidizing agent. Ozone has 150% of the oxidizing potential of chlorine and twice the oxidizing potential of bromine. Ozone has been shown to be much more effective than chlorine with a reaction time up to 10 times faster. Ozone also readily self-destructs into simple diatomic oxygen due to its inherent instability. Ozone oxidizes biological products and kills bacteria.

Catalytic ionization using ultraviolet light is known to produce a mixture of hydroxyl and hydroperoxide ions. Ionization devices which are used in automobiles to eliminate smoke and odors are known in the art to produce hydroxyl and hydroperoxide ions.

SUMMARY OF THE INVENTION

The invention relates to a method for deodorizing the clothing and apparatus of sportsmen, professional or non professional. More particularly, there is provided a method for removing human scent or any other foreign scent of clothing used by hunters before or during a hunt through the use of ozone or hydroxyl and hydroperoxide ions produced by ionization in a manner that would not cause irritation or injury to the user or equipment. Also, there is provided a method for removing fish odor from fishermen and their clothing and equipment while in the field including lures, tackle boxes and containers. The principal objective of the invention is the provision of a method for effectively removing human scent from clothing used by sportsmen.

It is another object of the invention to deodorize fish odor on fishermen.

It is yet another object of the invention to de-scent or deodorize sportsmen while out in the field by the use of ozone or hydroxyl and hydroperoxide ions.

Yet another object of the invention is to provide a method of deodorizing clothing with ozone so that it will not cause irritation or harm.

It is a further object of the invention to provide ozone in a compressed or generated form in a hand held container for application in the field by sportsmen.

Other objects and advantages of this invention will become apparent from the description of the preferred embodiments and the claims.

BRIEF DESCRIPTION OF THE PREFERRED EMBODIMENTS

According to the present invention there is provided a method for the de-scenting of clothing used by sportsmen by the use of an oxidizing gas, namely, ozone or by ionization with UV light to produce hydroxyl and hydroperoxide ions. More particularly, the clothing of hunters can be treated with ozone or the hydroxyl and hydroperoxide ions either at home or in the field by the application of a small amount of ozone or the hydroxyl and hydroperoxide ions in order to remove the human scent or any other foreign scent. Also, the clothing of fishermen can be treated with the oxidizing gas while in the field to remove the odor of fish.

According to one embodiment of the invention, the human scent can be eliminated from clothing by applying a low volume stream of an oxidizing gas comprising ozone or hydroxyl and hydroperoxide ions directly on the hunter while he is wearing a hunting outfit. The gaseous stream is applied by an ozone generator which is hand held or a catalytic ionizer containing UV light and easily transported by the hunter. The gaseous stream can be applied directly to the clothing being worn by the hunter in an open atmosphere so as to be quickly diluted after it is passed over the clothing. Moreover, the gun or rifle or any other equipment, i.e. ammunition, arrows, scope, finders etc., of the hunter or sportsmen can be similarly treated to remove the gun or rifle or equipment odor.

In accordance with another embodiment of the invention, the clothing of the hunter can be treated before or after the hunt by placing the clothing in a container i.e. a sack, bag or box while passing the oxidizing gas into the container in order to remove any human or other scent foreign to that environment.

Another embodiment of the invention is that the instrument can be carried with the hunter or hung upwind of the body so it descents the human scent traveling downwind.

Also, some certain clothing is not cleaned after every use by the hunter or sportsmen such as gloves, hats, jackets, boots, and need to be deodorized and decontaminated before next use.

According to a further embodiment of the invention, the odor of fish can be eliminated from a fisherman's clothing, body or equipment by the direct application of a stream of ozone gas or hydroxyl and hydroperoxide ions to the site of the fish odor. Additionally, a fisherman's hands can be deodorized with ozone so as to remove the fish odor without causing irritation.

Each of the methods can be practiced in the open in the field of sports activity utilizing a low volume gas generator. The clothing is not decolorized as in applications involved in high volumes of ozone as found in the garment industry where ozone is used to both de-size and/or decolorize denim garments. The oxidizing gas may be used alone or diluted with air as when packaged in a compressed gas form. Ozone which is produced by generators in amounts up to 8000 mg/hr can be compressed or diluted with an inert gas and compressed into small containers.

It is understood that the term "sportsmen" is meant to include those individuals who may hunt with a camera or who merely enter an environment to observe animals in their habitat.

Additionally, the term "fishermen" includes those individuals who handle the fish caught by others.

Hydroxyl and hydroperoxides are produced in a process known as "Radiant Catalytic Ionization" which utilizes ultra violet light which activates a photocatalytic target.

Small ozone generators such as those producing 1 to 25 lbs. of ozone per day can be utilized. Also the ozone can be applied from compressed ozone-filled containers similar to compressed air.

Low volume ozone generators which generate up to 65 mg/hr of ozone and are portable as well as high volume ozone generators are currently sold by EcoQuest International of Greeneville, Tenn. which also sells the generators of hydroxyl and hydroperoxide ions.

It will be appreciated by persons skilled in the art that numerous variations and/or modifications may be made to the invention without departing from the spirit or scope of the invention as broadly claimed.

What is claimed is:

1. A method of eliminating scent from a hunter's body, clothes worn by the hunter, and equipment used by the hunter, comprising:
   providing a portable ozone generator for discharging a stream of ozone;
   transporting the portable ozone generator by the hunter into the field;
   hanging the portable ozone generator in an open atmosphere in which the hunter and game animals are present and applying the stream of ozone directly on the hunter, clothing worn by the hunter, and equipment used by the hunter;
   wherein applying the stream of ozone directly on the hunter, clothing worn by the hunter, and equipment used by the hunter occurs in the open atmosphere to deodorize the hunter, clothing worn by the hunter, and equipment used by the hunter to eliminate human scent and other scent foreign to the open atmosphere such that deodorized air travels downwind of the hunter.

2. The method of claim 1 wherein the equipment comprises a rifle.

3. The method of claim 1 wherein the equipment comprises ammunition.

4. The method of claim 1 wherein the equipment comprises arrows.

5. The method of claim 1 wherein the ozone is diluted with air and packaged in a compressed gas form.

6. The method of claim 1 wherein the ozone generator produces 1 to 25 lbs. of ozone per day.

7. The method of claim 1 wherein the ozone generator produces up to 65 mg/hr of ozone.

8. The method of claim 1 wherein the portable ozone generator is hung upwind of the hunter.

9. A method of eliminating scent from a hunter's body, clothes worn by the hunter, and equipment used by the hunter, comprising:
   providing a portable oxidizing gas generator for discharging a stream of oxidizing gas;
   transporting the portable oxidizing gas generator by the hunter into the field;
   hanging the portable oxidizing gas generator in an open atmosphere in which the hunter and game animals are present and applying the stream of oxidizing gas directly on the hunter, clothing worn by the hunter, and equipment used by the hunter;
   wherein applying the stream of oxidizing gas directly on the hunter, clothing worn by the hunter, and equipment used by the hunter occurs in the open atmosphere to deodorize the hunter, clothing worn by the hunter, and equipment used by the hunter to eliminate human scent and other scent foreign to the open atmosphere such that deodorized air travels downwind of the hunter.

10. The method of claim 9 wherein the equipment comprises a rifle.

11. The method of claim 9 wherein the equipment comprises ammunition.

12. The method of claim 9 wherein the equipment comprises arrows.

13. The method of claim 9 wherein the oxidizing gas is diluted with air and packaged in a compressed gas form.

14. The method of claim 9 wherein the oxidizing gas generator produces 1 to 25 lbs. of oxidizing gas per day.

15. The method of claim 9 wherein the oxidizing gas generator produces up to 65 mg/hr of oxidizing gas.

16. The method of claim 9 wherein the portable oxidizing gas generator is hung upwind of the hunter.

17. The method of claim 9 wherein the oxidizing gas comprises ozone.

18. The method of claim 9 wherein the oxidizing gas comprises hydroxyl and hydroperoxide.

* * * * *